US011723871B2

(12) United States Patent
Smit et al.

(10) Patent No.: US 11,723,871 B2
(45) Date of Patent: Aug. 15, 2023

(54) POLY(METH)ACRYLIC ACID POPCORN POLYMERIZATES AS DISINTEGRANTS FOR TABLETS

(71) Applicant: BASF SE, Ludwigshafen (DE)

(72) Inventors: Theo Smit, Ludwigshafen (DE);
Matthias Karl, Ludwigshafen (DE);
Felicitas Guth, Ludwigshafen (DE);
Maximilian Angel, Kasendorf (DE);
Karl Kolter, Ludwigshafen (DE);
Frank Schmidt, Ludwigshafen (DE);
Maximilian Blochberger-Claus, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/052,934

(22) PCT Filed: May 15, 2019

(86) PCT No.: PCT/EP2019/062407
§ 371 (c)(1),
(2) Date: Nov. 4, 2020

(87) PCT Pub. No.: WO2019/219717
PCT Pub. Date: Nov. 21, 2019

(65) Prior Publication Data
US 2021/0251905 A1 Aug. 19, 2021

(30) Foreign Application Priority Data
May 16, 2018 (EP) ..................................... 18172745

(51) Int. Cl.
*A61K 9/20* (2006.01)

(52) U.S. Cl.
CPC .......... *A61K 9/2027* (2013.01); *A61K 9/2031* (2013.01)

(58) Field of Classification Search
CPC ... A61K 9/2027; A61K 9/2031; A61K 9/2846
See application file for complete search history.

(56) References Cited

U.S. PATENT DOCUMENTS

| 4,658,002 A * | 4/1987 | Tschang ................. C08F 26/10 526/264 |
| 5,599,898 A * | 2/1997 | Hartmann ................ B01J 20/26 521/25 |
| 6,254,892 B1 * | 7/2001 | Duccini ............... A61K 9/2027 424/488 |
| 6,677,417 B2 | 1/2004 | Meffert et al. |
| 2006/0052559 A1 * | 3/2006 | Gomez .................. C08F 12/30 526/264 |
| 2011/0015280 A1 | 1/2011 | Kim et al. |

FOREIGN PATENT DOCUMENTS

| DE | 4237439 A1 | 5/1994 | |
| DE | 10011137 A1 | 9/2001 | |
| EP | 0177812 A1 | 4/1986 | |
| EP | 972825 A2 * | 1/2000 | ......... C11D 17/0073 |
| EP | 0972825 A2 | 1/2000 | |
| EP | 1035196 A1 | 9/2000 | |
| EP | 1167433 A1 | 1/2002 | |
| EP | 1314776 A1 | 5/2003 | |
| JP | 2009-503136 A | 1/2009 | |

OTHER PUBLICATIONS

Breitenbach, et al., "Acrylic acid popcorn polymers", Die Makromolekulare Chemie, vol. 175, Issue 9, Sep. 1974, pp. 2597-2604.
Breitenbach, et al., "Acrylsäure?popcornpolymere, 2†. Oberflächenstruktur der glasigen und der popcorn?polymeren", Die Makromolekulare Chemie, vol. 177, Issue 9, Sep. 1976, pp. 2787-2792.
Khan, et al., "Water-sorption properties of tablet disintegrants", Journal of Pharmaceutical Sciences, vol. 64, Issue 3, Mar. 1975, pp. 447-451.
International Application No. PCT/EP2019/062407, International Search Report, dated Jul. 17, 2019.

* cited by examiner

*Primary Examiner* — Robert A Wax
*Assistant Examiner* — William Craigo
(74) *Attorney, Agent, or Firm* — Marshall, Gerstein & Borun LLP

(57) ABSTRACT

The use of powder-form, crosslinked, water-insoluble, low-swelling polyacrylates as disintegrants for solid pharmaceutical dosage forms.

16 Claims, No Drawings

POLY(METH)ACRYLIC ACID POPCORN POLYMERIZATES AS DISINTEGRANTS FOR TABLETS

CROSS-REFERENCE TO RELATED APPLICATIONS

This is the U.S. national phase of International Application No. PCT/EP2019/062407, filed May 15, 2019, which claims the benefit of European Patent Application No. 18172745.4, filed May 16, 2018.

DESCRIPTION

The present invention relates to the use of water-insoluble, non-swelling poly(meth)acrylic acid popcorn polymers as disintegrants for pharmaceutical tablets.

Acrylic acid popcorn polymers are known per se, see J. W. Breitenbach et al. in "Die Makromolekulare Chemie" [Macromolecular Chemistry], 175, 2597-2604 (1974) or in J. W. Breitenbach, "Makromolekulare Chemie" [Macromolecular Chemistry], 177, 2787-2792 (1976), although without the uses thereof being described.

EP-A 177 812 describes the production of popcorn polymers based on carboxylic acids and derivatives thereof, for example acrylic acid derivatives, by polymerization in a fixed bed using popcorn polymers obtained from N-vinyl-2-pyrrolidone as seed material. Such polymers are intended for use as adsorbents or as formulation aids for plant protection agents, with the adsorption of tannins specifically described.

The use of disintegrants to improve the disintegration and the dissolution rate of tablets has been long known.

A disintegrant of proven utility for this purpose is crosslinked polyvinylpyrrolidone, also known as PVP or crospovidone, as described for example in U.S. Pat. No. 6,677,417. This is a popcorn polymer. Crospovidone has excellent disintegrant properties, but is expensive.

More inexpensive commercially available disintegrants are, for example, croscarmellose-Na, which is the sodium salt of a crosslinked carboxymethyl starch, or sodium starch glycolate, although their disintegrant effect is less pronounced than that of crospovidone.

The use as disintegrants of crosslinked polyacrylic acid of the cation exchanger resin type is also known. Such resins are known from pharmacopeias also as polacrilin potassium NF. An example of a commercially available product of this type is Amberlite™ IRP 88 from Dow Chemicals, which is based on methacrylic acid crosslinked with divinylbenzene. The disintegrant effect is ascribed here to swelling behavior associated with hydration. However, aqueous suspensions of such polacrilin resins have relatively high pH values, which means that their suitability for hydrolysis-sensitive active compounds is low.

For the use of starch derivatives or polacrilin resins as disintegrants, see also K. A. Khan and C. T. Rhodes, J. of Pharmaceutical Sciences, Vol. 64, No. 3, 447-451 (1975).

EP-A 1035 196, EP-A 1314776, and EP-A 972825 disclose crosslinked polyacrylates and the use thereof as disintegrants for pellet formulations, with the crosslinked polyacrylates intended to have a gelation time of 30 seconds or less. However, crosslinked polyacrylates that undergo gelation with such rapidity are disadvantageous as regards the disintegration time of tablets.

The object of the present invention was to find a tablet disintegrant that has a disintegrant effect of comparable efficacy to crospovidone but is more inexpensively obtainable, has a better disintegrant effect than comparably inexpensive products such as starch derivatives, and can also be used for hydrolysis-sensitive drug substances.

Accordingly, use has been found of water-insoluble, low-swelling polyacrylates as disintegrants for pharmaceutical dosage forms, especially tablets. For the purposes of the invention, "polyacrylates" refers to polymers based on acrylic or methacrylic acid or mixtures thereof.

It is also possible for polyacrylates to contain up to 20% by weight of comonomer structural elements. Comonomers may be selected from the group consisting of methacrylic esters such as methyl acrylate, methyl methacrylate, hydroxyethyl methacrylate, hydroxyethyl acrylate and ethyl acrylate, butyl acrylate, and 2-ethylhexyl acrylate.

Particular preference is given to polymers obtained from pure acrylic acid or methacrylic acid.

"Water-insoluble" in the context of the invention means that less than 1% (m/m) of the polymer is soluble in water at 20° C. and standard pressure. "Low-swelling" in the context of the invention means that the percent change in the polymer particle size in water compared with the change in particle size in hexadecane is less than 50%. The percent change in the polymer particle size can be determined in accordance with ISO 13320:2009, as described in more detail hereinbelow.

The polyacrylates used according to the invention are popcorn polymers.

The polymers used according to the invention additionally undergo gelation slowly. "Slow" means that the gelation time is at least more than 30 seconds. The gelation time can be carried out as known from the prior art. This involves determining the time until the vortex in a test liquid caused by stirring is no longer visible. The test liquid used is a 0.9% by weight sodium chloride solution.

The determination of the gelation time can be carried out as described in EP-A 1035196, [0028]. An aqueous solution of sodium chloride is prepared by dissolving analytical-grade sodium chloride in demineralized water to a salt concentration of 0.9% in the end solution. This aqueous 0.9% by weight sodium chloride solution is a reference test liquid ("test liquid") commonly used in the characterization of water-absorbing polymers. In a temperature-controlled room (20° C.), the water-absorbing crosslinked polyacrylate polymer (3 g) is transferred to a beaker (100 ml) having an internal diameter of 55 mm. The beaker is placed on an electric magnetic stirrer and a magnetic stirrer bar (45 mm×8 mm) is added for stirring. The stirring speed is adjusted to 600±20 rpm and the beaker is quickly filled with the test liquid (50 g). As soon as the addition of the test liquid is complete, this time is set as time zero, i.e. the time from which the gelation time is measured. The time measurements are stopped when, as a result of the formation of a gel by the water-absorbing polymer, stirring (stirring vortex) is no longer visible, i.e. a stirring vortex is no longer present. In the case of polymers that undergo rapid gelation, it may be necessary to reverse the order of addition to the beaker of the polymer and test liquid.

The poly(meth)acrylates used according to the invention are obtained by proliferating polymerization. This form of polymerization is also known as popcorn polymerization. Popcorn polymerization results in strong physical crosslinking as a result of interlooping of the polymer chains. The resulting polymer particles have a cauliflower-like structure.

The polymerization is preferably carried out in the absence of oxygen. "In the absence of oxygen" means that the oxygen concentration in the gas phase in the polymerization apparatus is so low that free radicals are able to form spontaneously without the spontaneously formed free radicals reacting immediately with oxygen. The absence of oxygen in the polymerization vessel can be achieved by flushing with inert gases such as nitrogen or argon.

In an embodiment of the invention, for complete removal of dissolved oxygen—within a range from 0.05% to 1% by weight based on the monomer mixture—it may also be advantageous to add a reductant such as sodium sulfite, sodium pyrosulfite, sodium dithionite, ascorbic acid or mixtures of reductants.

Preference is given to polymerization in the absence of an initiator. The free-radical polymerization is thus preferably not conducted as an initiated polymerization. When a free-radical initiator is used, this is only in a small amount (e.g. J. W. Breitenbach et al., "Die Makromolekulare Chemie" [Macromolecular chemistry], 175, 2597-2604 (1974)). In accordance with the invention, preference as disintegrants for solid pharmaceutical dosage forms is thus given to polyacrylates obtained through a spontaneous free-radical polymerization.

The polymerization is carried out in an aqueous medium. In a preferred embodiment, the polymerization is carried out as a precipitation polymerization from aqueous solution.

The concentration of the monomers in the aqueous solution may be from 5% to 90% by weight, preferably from 10% to 80% by weight, based on the total mixture. In a preferred embodiment, the monomer concentration is within a range from 10% to less than 40% by weight. In a particularly preferred embodiment, the monomer concentration is within a range from 10% to 30% by weight.

The polymers preferably additionally comprise a crosslinker. Suitable crosslinkers are all compounds having at least two ethylenically unsaturated double bonds in the molecule. Particularly suitable are methylenebisacrylamide, N,N'-acryloylethylene diamine, ethylene glycol diacrylate, ethylene glycol dimethacrylate, tetraethylene glycol acrylate, tetraethylene glycol dimethacrylate, diethylene glycol acrylate, diethylene glycol methacrylate, butanediol diacrylate, hexanediol dimethacrylate, trimethylolpropane triacrylate, divinyl dimethylmalonate, polyallyl ethers of sucrose, pentaerythritol triallyl ether, and mixtures of crosslinkers. Preference is given to crosslinkers that are at least trifunctional. Particular preference as crosslinkers is given to polyallyl ethers of sucrose and especially pentaerythritol triallyl ether.

The amount of crosslinker may be from 0.1% to 15% by weight, preferably from 0.5% to 10% by weight, particularly preferably from 1% to 5% by weight, based on the amount of monomer.

Metal ions can hinder popcorn formation. It could therefore be advantageous to carry out the polymerization in the presence of complexing agents. Examples of suitable complexing agents are the sodium salt of ethylenediaminetetraacetic acid and sodium pyrophosphate.

The polymerization temperature may be varied within a wide range, for example from about 20 to 200° C., preferably 50 to 150° C.

The polymerization is carried out under passage of an inert gas such as preferably nitrogen. The reaction pressure is adjusted as appropriate.

When seed material is used, the average particle size is within a range from 0.5 to 2 mm, determined by dynamic image analysis using a Camsizer P4 instrument from Retsch.

Preference is given to using popcorn polymers of acrylic acid. Particular preference is given to using popcorn polymers of acrylic acid having pentaerythritol triallyl ether as crosslinker.

The popcorn polymers may also be partially neutralized after the polymerization. Neutralization may be to a degree of 0 to 80%, depending on the field of application. Partial neutralization may be carried out using aqueous alkali solutions such as sodium hydroxide or potassium hydroxide solution (e.g. 1% to 25% by weight) or aqueous ammonia solutions (e.g. 1% to 25% by weight).

At the end of the polymerization, the popcorn polymer particles formed may be separated in the customary manner, for example by filtration or centrifugation.

The popcorn polymer particles may then be washed further with water to remove residual monomers or other contaminants. Aqueous polyacrylic acid popcorn suspensions have a residual acrylic acid content of less than 1% (determined by HPLC).

For use as a tablet disintegrant, the popcorn polymers are comminuted, preferably by milling. Suitable for this are customary milling devices used for the production of powders.

The polymer powders obtained by milling may then be fractionated by sieving. For use as a tablet disintegrant, preference is given to using the 100 to 200 µm sieve fractions.

In a preferred embodiment, sieve fractions having particle sizes of <100 µm, 100-200 µm, and 200-500 µm may also be used as seed material for initiating the formation of popcorn polymer particles. Such seed material may be used in amounts of 0.1% to 10% by weight based on the amount of monomer.

The tableting excipients consist first and foremost of fillers, binders, lubricants, and disintegrants. When the amount of active compound is very low (e.g. in the case of alkaloids, hormones, vitamins, etc.), fillers are used. These ensure that the tablet achieves the necessary size/necessary mass. Examples of those used are starches such as corn starch, potato starch, and wheat starch, lactose, microcrystalline celluloses, and—e.g. for lozenges—glucose, mannitol, and sorbitol. Binders (e.g. microcrystalline cellulose, polyvinylpyrrolidone, starches, etc.) additionally help with cohesion of the powder particles in a granulate and influence the solidity of the tablets. The purpose of lubricants (e.g. magnesium stearate, sodium stearyl fumarate, etc.) is to facilitate the expulsion of the tablet from the die by reducing friction between the inner wall of the die holes and the lateral surface of the tablets. They also reduce friction between the die holes and the lower punch, so as to prevent the lower punch from becoming jammed. The addition of disintegrants (e.g. crospovidone, croscarmellose-Na, Na starch glycolate, etc.) has a beneficial effect on pressing into stable tablets (stronger particle adhesion) and on the subsequent disintegration of the tablets in the gastrointestinal tract.

Direct tableting is understood as meaning the pressing of powder-form drug substance-excipient mixtures without pretreatment, as opposed to the pressing of granulates produced beforehand. Since this method is characterized by a low amount of work involved, direct tableting was employed in this test series.

It was surprisingly found that crosslinked poly(meth)acrylic acid products of the popcorn polymer type having a gelation time of >30 seconds perform better as disintegrants than crosslinked polyacrylates having a gelation time of <30 seconds, such as those known from the prior art.

The popcorn polymers used according to the invention also perform distinctly better as disintegrants than conventional commercial disintegrants based on derivatives of starch or cellulose. An additional advantage is the lower pH compared with Amberlite IRP 88 in the case of polymers having a low degree of neutralization. The polyacrylate popcorn polymers used according to the invention exhibit a good disintegrant effect without this affecting the stability of hydrolysis-sensitive active compounds too much.

What is very particularly advantageous, however, is the disintegrant effect of the polymers used according to the invention when no hydrolysis-sensitive active compounds are to be employed. In such cases, the degree of neutralization can be increased considerably, which surprisingly results in a significantly better disintegrant effect.

The present invention is accordingly characterized in particular by the following embodiments, with each embodiment encompassing all the features of the embodiments to which it relates.

Embodiment 1

The use of powder-form, crosslinked, water-insoluble, low-swelling polyacrylates as disintegrants for solid pharmaceutical dosage forms.

Embodiment 2

The use according to embodiment 1, wherein the polyacrylates are popcorn polymers.

Embodiment 3: The use according to embodiment 1 or 2, wherein "low-swelling" means that the percent change in the polymer particle size in water compared with the change in particle size in hexadecane is less than 50%.

Embodiment 4: The use according to any of embodiments 1 to 3, wherein the polyacrylates consist of structural elements of acrylic acid or methacrylic acid or mixtures thereof.

Embodiment 5: The use according to any of embodiments 1 to 4, wherein the polyacrylates contain up to 20% by weight of comonomer structural elements.

Embodiment 6: The use according to any of embodiments 1 to 5, wherein the comonomer structural elements are selected from the group consisting of (meth)acrylic esters such as methyl acrylate, methyl methacrylate, hydroxyethyl methacrylate, hydroxyethyl acrylate and ethyl acrylate, butyl acrylate, and 2-ethylhexyl acrylate.

Embodiment 7: The use according to any of embodiments 1 to 6, wherein powder-form polyacrylates having an average particle size within a range from 100 to 200 µm are used.

Embodiment 8: The use according to any of embodiments 1 to 7, wherein the polyacrylates additionally comprise structural elements from a crosslinker.

Embodiment 9: The use according to any of embodiments 1 to 8, wherein the crosslinker is selected from the group consisting of methylenebisacrylamide, N,N'-acryloylethylene diamine, ethylene glycol diacrylate, ethylene glycol dimethacrylate, tetraethylene glycol acrylate, tetraethylene glycol dimethacrylate, diethylene glycol acrylate, diethylene glycol methacrylate, butanediol diacrylate, hexanediol dimethacrylate, trimethylolpropane triacrylate, divinyl dimethylmalonate, polyallyl ethers of sucrose, pentaerythritol triallyl ether, and mixtures thereof.

Embodiment 10: The use according to any of embodiments 1 to 9, wherein the crosslinker is at least trifunctional.

Embodiment 11: The use according to any of embodiments 1 to 10, wherein the crosslinker is pentaerythritol triallyl ether.

Embodiment 12: The use according to any of embodiments 1 to 11, wherein the polyacrylates contain 0.1% to 15% by weight, based on the amount of acrylic acid or methacrylic acid, of a crosslinker.

Embodiment 13: The use according to any of embodiments 1 to 12, wherein the polyacrylates contain 0.5% to 10% by weight, based on the amount of acrylic acid or methacrylic acid, of a crosslinker.

Embodiment 14: The use according to any of embodiments 1 to 13, wherein the polyacrylates contain 1% to 5% by weight, based on the amount of acrylic acid or methacrylic acid, of a crosslinker.

Embodiment 15: The use according to any of embodiments 1 to 14, wherein the polyacrylates have a gelation time of less than 30 seconds.

Embodiment 16: The use according to any of embodiments 1 to 15, wherein the polyacrylates have a gelation time of less than 30 seconds and the gelation time is determined as the time after which the vortex in a test liquid caused by stirring is no longer visible, a 0.9% by weight sodium chloride solution being used as the test liquid.

Embodiment 17: A solid pharmaceutical dosage form in accordance with the use according to any of embodiments 1 to 16 that comprises, as a disintegrant, powder-form water-insoluble crosslinked polyacrylates.

Embodiment 18: A solid pharmaceutical dosage form according to embodiment 17 that comprises, as a disintegrant, polyacrylates in amounts of 0.1% to 50% by weight, preferably 0.2% to 20% by weight, more preferably 0.5% to 5% by weight, in particular 0.5% to 2% by weight, based on the total weight of the dosage form.

Embodiment 19: A process for producing the polyacrylates used according to any of embodiments 1 to 18 through free-radical polymerization in aqueous medium.

Embodiment 20: The process according to embodiment 19, through free-radical polymerization in aqueous medium, wherein the polymerization takes place without addition of a radical initiator.

Embodiment 21: The process according to either of embodiments 19 or 20, wherein the polymerization takes place in an aqueous medium in the absence of oxygen.

Embodiment 22: The process according to any of embodiments 19 to 21, wherein the polymerization takes place in an aqueous medium in the presence of a reductant.

Embodiment 23: The process according to any of embodiments 19 to 22, wherein the polymerization takes place in an aqueous medium in the presence of a reductant and the reductant is selected from the group consisting of sodium sulfite, sodium pyrosulfite, sodium dithionite, ascorbic acid or mixtures thereof.

Embodiment 24: The process according to any of embodiments 19 to 23, wherein the polymerization takes place in an aqueous medium in the presence of 0.05% to 1% by weight of a reductant.

Embodiment 25: The process according to any of embodiments 19 to 24, wherein the polymerization is carried out in the presence of seed material, wherein the seed material used consists of particle fractions of the polyacrylates used according to the invention.

Embodiment 26: The process according to any of embodiments 19 to 25, wherein the polymerization is carried out in the presence of complexing agents.

Embodiment 27: The process according to any of embodiments 19 to 26, wherein the polymerization is carried out in the presence of complexing agents such as the sodium salt of ethylenediaminetetraacetic acid or sodium pyrophosphate.

Embodiment 28: The process according to any of embodiments 19 to 27, wherein the polyacrylates are partially neutralized.

Embodiment 29: The process according to any of embodiments 19 to 28, wherein the polyacrylates are partially neutralized with aqueous alkali solutions such as sodium hydroxide or potassium hydroxide solution or aqueous ammonia solutions.

Embodiment 30: The process according to either of embodiments 28 or 29, wherein the polyacrylates are adjusted to a degree of neutralization of up to 80%.

EXAMPLES

Pentaerythritol triallyl ether (PETAE) is commercially available from Perstorp GmbH. Manufacturer's data: Diallyl ether content: 4.0-16.0%, triallyl ether content: 75.0-84.0%, and tetraallyl ether content: 5.0-12.0%.

Demin. water=demineralized water

Production of Popcorn Polymer A:

A 3-liter glass reactor equipped with a stirrer, a reflux condenser, and metering devices was charged with 1086 g of deionized water, 450 g of acrylic acid, 22.5 g of pentaerythritol triallyl ether (PETAE), and 2.25 g of sodium pyrophosphate and heated to 50° C. with stirring at a stirrer speed of 180 rpm. During the heating period up to the end of the polymerization, nitrogen was passed through the solution, this being introduced into the reaction mixture by means of a tube extending down to the base of the stirring apparatus. The flow rate was 20 L/hour. Once the temperature of the reaction mixture had reached 50° C., 1.04 g of sodium dithionite was added. The mixture was held at 50° C. The first popcorn polymer particles were formed 60 minutes after adding the sodium dithionite, whereupon heat was evolved, which lasted a further 70 minutes. Stirring of the mixture was continued during this time. The aqueous suspension was then stirred for one hour further at 50° C. and filtered off. The polymer was washed with three 2000 ml portions of water to remove contaminants such as soluble polymer and residual monomers. The product was dried under reduced pressure for 12 hours at 75° C. The yield of popcorn polymer was 93%. The popcorn polymer exhibited a very heterogeneous particle size distribution and comprised particles of 5-10 cm in size. The product was milled with a Vorwerk Thermomix for 4 minutes at maximum speed and then sieved. The 100-200 μm sieve fraction was tested as a disintegrant.

Production of Popcorn Polymer B:

Popcorn polymer B was produced in analogous manner to the production of popcorn polymer A, but with 4.50 g of the 100-200 μm sieve fraction of polymer A added as seed to the initial charge. The first popcorn polymer particles were discernible after just 10 minutes. The yield of popcorn polymer was 91%. The use of seed resulted in a distinctly finer product having an average particle size in the region of 1 mm.

Production of Popcorn Polymer C:

Popcorn polymer C was produced in analogous manner to the production of popcorn polymer B, but was produced without the use of 2.25 g of sodium pyrophosphate. The first popcorn polymer particles were discernible after 10 minutes. The yield of popcorn polymer was 88%.

Production of Popcorn Polymer D:

Popcorn polymer D was produced in analogous manner to the production of popcorn polymer A, but with 2.25 g of a 200-500 μm sieve fraction of polymer A added as seed to the initial charge. The first popcorn polymer particles were discernible after 20 minutes. The yield of popcorn polymer was 94%.

Production of Popcorn Polymer E:

Popcorn polymer E was produced in analogous manner to the production of popcorn polymer, but with the reactor initially charged with only 90 g of acrylic acid. The remaining 360 g of acrylic acid was metered in over a two-hour period at a constant addition rate once the first popcorn particles had formed, which occurred 10 minutes after addition of the sodium dithionite. The yield of popcorn polymer was 95%.

Production of Popcorn Polymer F:

Popcorn polymer F was produced in analogous manner to the production of popcorn polymer A, but with 4.50 g of the <100 μm sieve fraction of polymer A added as seed to the initial charge. The first popcorn polymer particles were discernible after 30 minutes. The yield of popcorn polymer was 92%.

Production of Popcorn Polymer G:

Popcorn polymer G was produced in analogous manner to the production of popcorn polymer F, but with partial neutralization of the polymer. Partial neutralization was effected by adding 300 g of a 25% by weight aqueous sodium hydroxide solution to the aqueous suspension after the polymerization, followed by stirring at room temperature for one hour. The first popcorn polymer particles were discernible after 30 minutes. The yield of popcorn polymer was 91%.

Production of Popcorn Polymer H:

Popcorn polymer H was produced in analogous manner to the production of popcorn polymer B, but with 450 g of methacrylic acid used instead of 450 g of acrylic acid. The first popcorn polymer particles were discernible after 23 hours. The reaction mixture was then stirred for 8 hours at 80° C. Filtration, drying, and milling was in accordance with 689. The yield of popcorn polymer was 62%.

Production of Popcorn Polymer I:

Popcorn polymer I was produced in analogous manner to the production of popcorn polymer B, but with partial neutralization of the polymer. Partial neutralization was effected by adding 420 g of a 25% by weight aqueous potassium hydroxide solution to the aqueous suspension after the polymerization, followed by stirring at room temperature for one hour. The first popcorn polymer particles were discernible after 30 minutes. The yield of popcorn polymer was 96%.

Production of Popcorn Polymer J:

Popcorn polymer J was produced in analogous manner to the production of popcorn polymer F, but using the following amounts of starting materials: 1050 g of deionized water, 250 g of acrylic acid, 12.5 g of PETAE, 1.25 of sodium pyrophosphate, 2.50 g of a <100 μm sieve fraction of polymer A as seed, and 0.58 instead sodium dithionite. The first popcorn polymer particles were discernible after 20 minutes. The yield of popcorn polymer was 85%.

Production of Popcorn Polymer K:

Popcorn polymer K was produced in analogous manner to the production of popcorn polymer J, but using 2.50 g of the 100-200 μm sieve fraction of polymer A as seed. The first popcorn polymer particles were discernible after 20 minutes. The yield of popcorn polymer was 76%.

Production of Popcorn Polymer L:

Popcorn polymer L was produced in analogous manner to the production of popcorn polymer B, but using the following amounts of starting materials: 1300 g of deionized water, 300 g of acrylic acid, 15.0 g of PETAE, 1.50 g of sodium pyrophosphate, 3.00 g of the 100-200 μm sieve fraction of polymer A as seed, and 0.69 g of sodium dithionite. The polymer was additionally partially neutralized.

Partial neutralization was effected by adding 200 g of a 25% by weight aqueous potassium hydroxide solution to the aqueous suspension after the polymerization, followed by stirring at room temperature for one hour. The first popcorn polymer particles were discernible after 35 minutes. The yield of popcorn polymer was 85%.

Production of Popcorn Polymer M:

Popcorn polymer M was produced in analogous manner to the production of popcorn polymer J, but using 2.50 g of the <100 μm sieve fraction of polymer A as seed and with partial neutralization of the polymer. Partial neutralization was effected by adding 167 g of a 25% by weight aqueous sodium hydroxide solution to the aqueous suspension after the polymerization, followed by stirring at room temperature for one hour. The first popcorn polymer particles were discernible after 30 minutes. The yield of popcorn polymer was 90%.

For Comparison: Production of Gel Polymer C1:

A 2-liter glass reactor equipped with a stirrer and a reflux condenser was charged at room temperature and under a nitrogen atmosphere with 605 g of deionized water, 400 g of acrylic acid, 20 g of PETAE, and 5 g of a 5% by weight aqueous hydrogen peroxide solution. The mixture was stirred at 180 rpm and heated to 30° C. A 25% by weight aqueous sodium hydroxide solution (266.6 g) was metered in over 20 minutes. This was followed by the addition of 28.2 g of an aqueous L(+)-ascorbic acid solution (0.2 g of L(+)-ascorbic acid in 28 g of water). A very pronounced evolution of heat and increase in viscosity were observed within a few seconds. The stirring speed was reduced to 20 rpm. The viscosity continued to increase and a homogeneous clear gel formed. The gel was stirred for two hours and then removed from the reactor, comminuted, and freeze-dried. The yield of gel polymer was 99%. The product was milled with a Vorwerk Thermomix for 4 minutes at maximum speed and then sieved. The 100-200 μm sieve fraction was tested as a disintegrant (Table 3).

Production of Placebo Tablets

All disintegration times reported hereinbelow were tested on placebo tablets obtained as follows:

Tablet Formulation (Direct Tableting):

467.50 mg of Ludipress LCE (96.5% lactose monohydrate, 3.5% polyvinylpyrrolidone (Kollidon® 30)), 30 mg of disintegrant (popcorn and gel polymers, Amberlite IRP 88, Ac-Di-Sol, Primojel, Kollidon CL), and 2.50 mg of magnesium stearate. All starting materials were sieved through a 0.8 mm mesh screen and mixed for 10 minutes in a Turbula mixer. Tablets were pressed at 18 kN on a Korsch XP1 eccentric press, at 6 and 12 kN in the case of some of these formulations. Disintegration times were determined using an Erweka ZT 74 (disintegration tester) in 0.08 N HCl (pH 1.1), phosphate buffer (pH 6.8), and demineralized water.

The measurement of the disintegration time with the Erweka ZT 74 was performed according to the following method: Fill a 1000 ml beaker (low-sided form) with 800 ml of the desired test medium (e.g. 0.08 N HCl, phosphate buffer, demineralized water), stand in a water bath, and thermally equilibrate at 36-38° C. Into each of the numbered tubes of the measurement basket is placed a tablet or capsule (sixfold determination per formulation) and the associated disk is laid on top of this. This measurement basket is suspended in the holder over the filled beaker and the measurement is started. The basket is moved up and down until the residual thickness of the tablet is only max. 0.2 mm in all tubes. The sensor issues a signal according to the distance of the inbuilt magnet inside the disk. When the sample has disintegrated, the smallest-possible distance will have been reached and the time is recorded. The end of the test is reached and the disintegration time determined when all the test specimens have disintegrated. The measurement basket then switches off automatically.

Determination of the Gelation Time

The gelation time is determined as described in EP-A 1035196, [0028]. The exact method is described above in the general description.

Determination of the particle size distribution (PSD) in hexadecane and water

The measurements were carried out using a Mastersizer 3000 (static light scattering/Fraunhofer diffraction) in accordance with ISO 13320:2009.

Method 1: Aqueous

The measurement unit for aqueous samples is the Hydro MV unit:

For the measurement in the Hydro unit, after the initialization step and the background measurement, the sample (microspatula) was added directly to the Hydro unit until the optimal laser obscuration of 2-15% had been reached. After addition of the sample, a wait time of approx. 30 seconds to allow the sample to disperse thoroughly was observed before starting the measurement. Parameters for analysis and evaluation in the Hydro MV unit:

Stirrer speed: 1500 rpm

Ultrasound: Without

Evaluation model: Fraunhofer

Analysis model: Universal

| Sample | Medium water Laser obscuration (%) |
|---|---|
| Gel polymer C1 | 6.49 |
| Polymer M | 9.33 |

Method 2: in Hexadecane

The measurement unit for hexadecane is the SV cell unit:

For the measurement in the SV cell unit, after initialization and the background measurement, the sample (homogenize 1 spoon-spatula of sample with hexadecane in a 10 ml screw-cap bottle) was added dropwise until the optimal laser obscuration of 2-15% had been reached. After introducing the cell measurement unit into the instrument, the measurement was started. Parameters for analysis and evaluation in the SV cell unit:

Stirrer speed: 1500 rpm

Ultrasound: Without

Evaluation model: Fraunhofer

Analysis model: Universal

| Sample | Hexadecane Laser obscuration (%) |
|---|---|
| Gel polymer C1 | 6.78 |
| Polymer M | 12.50 |

The results are listed in the table below.

TABLE 1

Comparison of disintegration times of the tablet formulation of commercial disintegrants with the inventive polymer M

| Disintegrant | Disintegration time pH 1.1 [min:s] | Disintegration time pH 6.8 [min:s] | Disintegration time Demin. water [min:s] |
| --- | --- | --- | --- |
| Ac-Di-Sol (croscarmellose-Na) | 2:56 | 3:50 | 2:39 |
| Primojel (Na starch glycolate) | 2:45 | 3:38 | 3:32 |
| Kollidon ® CL (crospovidone) | 1:15 | 1:54 | 1:12 |
| Polymer M | 2:09 | 2:35 | 2:12 |

The polyacrylic acid popcorn polymer M performed better than inexpensive disintegrant products such as Ac-Di-Sol and Primojel that are currently on the market.

TABLE 2

Gelation time, PSD in hexadecane/water and disintegration time: Popcorn vs. gelpolymerization

| Disintegrant | Gelation time* [min:s] | Particle size in hexadecane [μm] | Particle size in water [μm] | Change in particle size $C_{16}H_{34} \rightarrow H_2O$ | Disintegration time pH 1.1 [min:s] |
| --- | --- | --- | --- | --- | --- |
| Gel polymer C1 | <0:10 | 110 | 475 | +332% | 3:18 |
| Polymer M | >10:00 | 124 | 165 | +33% | 2:09 |

*Described in EP1035196 B1 (page 5, [0028])

Although the polymers were produced using identical amounts of monomer and crosslinker, they differed considerably. The results in Table 2 show that the gel polymer swells rapidly and substantially in water. The popcorn polymer swells only little and very slowly, but shows a better disintegrant effect.

In addition, the disintegrant effect of inventive polymers was compared with the disintegrant effect of the commonly used commercial Amberlite™ IRP 88. The results are listed in Table 3.

TABLE 3

Neutralization, pH, and disintegration time: Popcorn vs. Amberlite

| Disintegrant | Neutralization [mol % carboxylic acid groups] | pH (1% in water) | Disintegration time pH 1.1 [min:s] | Disintegration time pH 6.8 [min:s] | Disintegration time Demin. water [min:s] |
| --- | --- | --- | --- | --- | --- |
| Amberlite IRP 88 | 60* | 9.7 | 2:25 | 2:24 | 2:42 |
| Polymer K | 0 | 3.4 | 1:54 | 2:00 | 1:40 |
| Polymer M | 30 | 7.7 | 2:09 | 2:35 | 2:12 |
| Polymer L | 50 | 9.0 | 1:14 | 1:01 | 0:48 |

*calculated from determination of the water content and elemental analysis (potassium and oxygen)

TABLE 4

Determination of the disintegration times of tablet formulations at different pH values

| Polymer | Disintegration time pH 1.1 [min:s] | Disintegration time pH 6.8 [min:s] | Disintegration time Demin, water [min:s] |
| --- | --- | --- | --- |
| A | 1:34 | 1:32 | 1:12 |
| B | 1:18 | 1:42 | 1:13 |
| C | 1:28 | 1:42 | 1:21 |
| D | 2:33 | 2:06 | 1:28 |
| E | 2:07 | 2:12 | 1:52 |
| F | 1:30 | 1:32 | 1:13 |
| G | 1:54 | 2:11 | 1:56 |
| H | 3:44 | 4:30 | 3:55 |
| 1 | 2:29 | 1:45 | 1:52 |
| J | 2:00 | 2:09 | 1:41 |
| K | 1:54 | 2:00 | 1:40 |
| L | 1:14 | 1:01 | 0:48 |
| M | 2:09 | 2:35 | 2:12 |

The invention claimed is:

1. A solid pharmaceutical dosage form comprising a disintegrant, wherein the disintegrant is a powder-form water-insoluble, low-swelling crosslinked polyacrylate, and wherein the polyacrylate is a popcorn polymer and has a gel time of greater than 30 seconds.

2. The dosage form according to claim 1, wherein the polyacrylate comprises structural elements of acrylic acid or methacrylic acid or mixtures thereof.

3. The dosage form according to claim 1, wherein the polyacrylate contains up to 20% by weight of comonomer structural elements.

4. The dosage form according to claim 1, wherein the comonomer structural elements comprise a (meth)acrylic ester.

5. The dosage form of claim 4, wherein the (meth)acrylic ester is selected from the group consisting of methyl acrylate, methyl methacrylate, hydroxyethyl methacrylate, hydroxyethyl acrylate and ethyl acrylate, butyl acrylate, and 2-ethylhexyl acrylate ester.

6. The dosage form according to claim 1, wherein powder-form polyacrylate has an average particle size within a range from 100 to 200 μm.

7. The dosage form according to claim 1, wherein the polyacrylate additionally comprises structural elements from a crosslinker.

8. The dosage form according to claim 7, wherein the crosslinker is at least trifunctional.

9. The dosage form according to claim 8, wherein the crosslinker is pentaerythritol triallyl ether.

10. The dosage form according to claim 8, wherein the polyacrylate comprises 0.1% to 15% by weight, based on the amount of acrylic acid or methacrylic acid, of the trifunctional crosslinker.

11. The dosage form of claim 10, wherein the polyacrylate comprises 0.5% to 10% by weight, based on the amount of acrylic acid or methacrylic acid, of the trifunctional crosslinker.

12. The dosage form of claim 10, wherein the polyacrylate comprises 1% to 5% by weight, based on the amount of acrylic acid or methacrylic acid, of the trifunctional crosslinker.

13. The dosage form of claim 1 wherein the crosslinked polyacrylate is partially neutralized.

14. A solid pharmaceutical dosage form comprising a disintegrant, wherein the disintegrant is a powder-form, water-insoluble, low-swelling crosslinked polyacrylate consisting of
- (a) structural elements selected from the group consisting of acrylic acid, methacrylic acid, and a mixture thereof;
- (b) up to 20% by weight of (meth)acrylic ester comonomer structural elements; and
- (c) 0.5 to 10% by weight, based on the amount of structural elements (a) of a trifunctional crosslinker;
wherein the polyacrylate is a popcorn polymer and has a gel time of greater than 30 seconds.

15. The dosage form of claim 14, wherein the (meth) acrylic ester comonomer is selected from the group consisting of methyl acrylate, methyl methacrylate, hydroxyethyl methacrylate, hydroxyethyl acrylate and ethyl acrylate, butyl acrylate, and 2-ethylhexyl acrylate ester.

16. The dosage form of claim 14 wherein the trifunctional crosslinker is pentaerythritol triallyl ether.

* * * * *